(12) United States Patent
Sinha

(10) Patent No.: US 8,333,198 B2
(45) Date of Patent: *Dec. 18, 2012

(54) BREATHING CIRCUIT

(76) Inventor: Shailendra K. Sinha, Hewlett, NY (US)

( * ) Notice: Subject to any disclaimer, the term of this patent is extended or adjusted under 35 U.S.C. 154(b) by 8 days.

This patent is subject to a terminal disclaimer.

(21) Appl. No.: 13/008,829

(22) Filed: Jan. 18, 2011

(65) Prior Publication Data

US 2011/0108029 A1 May 12, 2011

Related U.S. Application Data

(63) Continuation of application No. 11/786,665, filed on Apr. 12, 2007, now Pat. No. 7,900,633.

(51) Int. Cl.
*A61M 11/00* (2006.01)

(52) U.S. Cl. ......... 128/207.14; 128/207.16; 128/200.24; 128/205.13

(58) Field of Classification Search .......... 128/207.14–207.16, 204.18, 205.13, 128/205.17, 200.24
See application file for complete search history.

(56) References Cited

U.S. PATENT DOCUMENTS

| | | | |
|---|---|---|---|
| 3,556,097 A | 1/1971 | Wallace | |
| 4,088,131 A | 5/1978 | Elam et al. | |
| 4,333,451 A | 6/1982 | Paluch | |
| 4,453,543 A | 6/1984 | Kohnke et al. | |
| 4,463,755 A | 8/1984 | Suzuki | |
| 4,543,951 A | 10/1985 | Phuc | |
| 4,702,243 A | 10/1987 | Smith | |
| 5,311,861 A | 5/1994 | Miller | |
| 5,485,835 A | 1/1996 | Vande Streek et al. | |
| 6,508,250 B1 | 1/2003 | Esnouf | |
| 6,874,500 B2 | 4/2005 | Fukunaga et al. | |
| 2001/0032646 A1 | 10/2001 | Christopher | |
| 2002/0112730 A1 | 8/2002 | Dutkiewicz | |
| 2003/0051730 A1 | 3/2003 | Thuener | |
| 2003/0051731 A1 | 3/2003 | Be'eri et al. | |
| 2004/0173214 A1 | 9/2004 | Tinker | |
| 2005/0098177 A1 | 5/2005 | Haj-Yahya et al. | |

OTHER PUBLICATIONS

Anesthesia Breathing Circuits by M Ravi Shankar, MD at http://www.capnography.com/Circuits/breathingcircuits.htm.

*Primary Examiner* — Steven Douglas
(74) *Attorney, Agent, or Firm* — Harold G. Furlow, Esq.

(57) ABSTRACT

A breathing circuit is described for the supplying of low pressure oxygen to a patient that is at risk of hypoxia. The breathing circuit includes a patent airway maintaining device, a first tube that includes a substantially rigid elbow and connectors and a flexible tubular extension. An inflatable bag is coupled to the first tube and has a pressure relief valve that exhausts into the atmosphere. A second tube has a first end that terminates in proximity to the patent airway maintaining device and a second opposed end that terminates external to the first tube. A third tube connects an external source of oxygen to the second tube. A method for an oxygen breathing circuit is also described that further includes the use of a carbon dioxide monitor and the inflatable bag for assisted breathing. The breathing circuit uses only non-metallic polymer or composite type materials.

15 Claims, 2 Drawing Sheets

BREATHING CIRCUIT

This application is a continuation of and claims priority to U.S. Utility patent application Ser. No. 11/786,665 filed Apr. 12, 2007, now U.S. Pat. No. 7,900,633 the disclosure of which is incorporated by reference herein and made a part of this application.

BACKGROUND OF THE INVENTION

1. Field of the Invention

The present invention relates to breathing circuits and more specifically to medical applications of low pressure oxygen breathing circuits.

2. Description of the Related Art

An increasing number of surgical procedures are being performed in doctor's offices. This in turn creates many challenges that have to be faced every day in the field of anesthesia. Anesthesia machines are one major type of anesthesia care and include assisted and/or artificial ventilation systems that provide an artificial atmosphere to a patient. These machines supply patients with fresh gases for breathing and remove expiratory waste gases. Fresh gases include inhalation anesthesia agents in combination with other gases, such as oxygen. Anesthesia is typically supplied continuously at flow rates between four and eight liters per minute.

The conduits that supply and remove the artificial atmosphere are commonly referred to as breathing circuits and have a variety of well known configurations such as, for example, those of the Mapleson and Bain breathing circuits. Anesthesia machines employ specialized anesthesia breathing circuits to deliver the fresh gases at high pressures. These breathing circuits have evolved into breathing circuit systems that use many conventional and standardized devices. Conventional devices as defined herein are devices approved for use in medical applications. Standard or standardized devices are those devices that have specific mechanical properties that have become widely used in the industry. For example, standard sized diameters tubes for breathing circuits and standard interfaces for connectors.

Anesthetizations are inherently complex procedures that are vulnerable to a wide range of problems. For example, medical staffs cannot wholly trust that patients have complied with their pre-anesthesia instructions and have arrived for their surgical procedure in a proper condition. During the surgical procedure, a slight movement of the patient's body can create a major disaster and result in permanent damage to the patient's body. Concerns such as these drive a strong preference by surgeons for well controlled patients in deep sedation.

Deep sedation, however, poses a number of risks including an increased likelihood that the patient's breathing will be interrupted. For example, deep sedation causes the patient's muscles to relax, including those surrounding the patient's airway and these muscles can restrict the airway. Thus, a patient's airways have to be constantly monitored for carbon dioxide build-up and/or maintained in the open position in order to prevent any breathing interruption. When the airway closes, the flow of fresh gases is interrupted, the patient can quickly reach a state of hypoxia and permanent damage to the patient.

Traditionally, most anesthesiologists are hesitant to implement the technique of providing a patent airway maintaining device to patients where deep sedation is required in an office procedure. In contrast, for the safety of the patients' airway, the Anesthesia Patent Safety Foundation requires that if a patient is under deep sedation, the airway must be made secure and an exhale carbon dioxide monitor as well as an oxygen saturation monitor must also be used. These measures are only possible when the patient's airway is secured by a patent airway maintaining device. The reality is, however, due to the lack of funding and poor planning, many doctors' offices are not always in full compliance with the requirements of the Anesthesia Patent Safety Foundation.

In many situations, however, anesthesia machines are not available for deep sedation due to their size, expense, particular concerns about the patient, cost or time constraints and a patient's airway is at risk. In these situations, intravenous narcotics and sedatives can be used to achieve deep sedation. While deep sedation using anesthesia machines typically requires the use of a patent airway device, intravenous deep sedation does not always use a patent airway device and as a result can have amplified risks. Deep sedative drugs depress the breathing center in the brain, which depresses respiration and suppresses swallowing reflexes. A further reduction in the patient's already shallow breathing can easily occur and is not necessarily readily detectable. This can lead to a carbon dioxide build up in the patient's body and patient may develop acidosis.

Deep sedation is also commonly used in conjunction with diagnostic equipment such as MRIs and radiographic machines. Diagnostic procedures using these machines require a completely relaxed and cooperative patient. This is not possible without the help of sedative drugs. Thus, usually non-MRI or other radiographic procedures require patients to be intubated or placed on a ventilator with intravenous sedative agents. The inability of the MRI procedure to accommodate metals, limits the ability of ventilators to be employed with patients. This creates a serious risk, since a deep sedative drug depresses respiration and swallowing reflexes. If the airway is not maintained, the patient can become hypoxic or aspirate in this situation as well.

In contrast to anesthesia breathing circuits, oxygen breathing circuits solely supply oxygen to patients and can be as simple as a source of oxygen connected to a face mask. Within this broad range of anesthesia and oxygen devices, however, there is a gap in which patients are at risk: there is a need for a breathing circuit that can intubate and supply low pressure oxygen to patients where there is an inherent risk of hypoxia with or without anesthesia. This at risk area of patients includes patients that are anesthetized without an anesthesia machine that are breathing normally. Another area of risk is those patients that are responsive, but not breathing normally. Still another area of risk is patients that are not anesthetized that are unresponsive and/or breathing abnormally due to trauma, for example.

An oxygen breathing circuit is needed that supplies low flow rates of oxygen directly into an airway maintaining device of a patient that has a low flow resistance, reduces dead space, does not interfere with diagnostic machines and can selectively provide assisted ventilation.

SUMMARY OF THE INVENTION

An oxygen breathing circuit is described that provides low pressure oxygen to a patient at risk of hypoxia. The oxygen breathing circuit comprises a patent airway maintaining device, a first tube, an inflatable bag and an external source of oxygen.

The first tube is a fluid tight conduit. The first tube includes a distal elbow and a proximal flexible tubular extension. A distal end portion of the elbow includes a distal connector and a proximal end portion of the flexible tubular extension includes a proximal connector. The distal connector couples to a proximal end portion of the patent airway maintaining device. The flexible tubular extension is both axially and radially flexible and has a cross-sectional diameter that does not substantially reduce during axial flexing. The flexible tubular extension is fixedly or permanently connected to a proximal end portion of the elbow and on the opposing end to the proximal connector. The flexible tubular extension has an abbreviated length. The elbow, proximal connector and distal connector are fabricated of a substantially rigid medical grade non-metallic material such as hard medical grade polymer or composite, for example. The flexible tubular extension is fixedly connected to the elbow and the second connector.

A second tube is connected to the first tube. The second tube has a first terminal end external to the first tube and an opposed second terminal end that is within the elbow and in proximity to the first connector. A breathing bag couples to the second connector and is in fluid communication with the patent airway maintaining device. The breathing bag includes a pressure release valve. A third tube couples an external source of oxygen to the second tube. The external source of oxygen supplies low pressure oxygen to the first tube.

The oxygen breathing circuit can include a humidification filter that is connected in-line with the breathing circuit between the patent airway maintaining device and the first tube. The oxygen breathing circuit can also include a carbon dioxide monitor that is in fluid communication with the breathing circuit. The flexible tubular extension is a ribbed silicone polymer based tube. The flexible tubular extension includes a substantially rigid polymer proximal end portion that is a connector. The abbreviated length of the flexible tube is approximately three inches. The patent airway maintaining device can be an endo-tracheal tube. The patent airway maintaining device can also be a laryngeal mask airway. The external source of oxygen supplies oxygen at a flow rate of approximately two liters per minute.

A method is also disclosed for providing low pressure oxygen to a patient at risk for hypoxia using an oxygen breathing circuit. The method comprising providing an oxygen breathing circuit having a patent airway maintaining device a first tube that is a fluid tight conduit, an inflatable bag and an external source of oxygen. The first tube includes a distal elbow and a proximal flexible tubular extension. A distal end portion of the elbow includes a distal connector and a proximal end portion of the flexible tubular extension includes a proximal connector. The distal connector attaches to a proximal end portion of the patent airway maintaining device. The flexible tubular extension is axially and radially flexible and has a cross-sectional diameter that does not substantially reduce during axial flexing. The flexible tubular extension is fixedly connected to a proximal end portion of the elbow and terminates in the proximal connector. The flexible tubular extension has an abbreviated length. The elbow, proximal connector and distal connector fabricated of a substantially rigid medical grade non-metallic material. The flexible tubular extension is fixedly connected to the elbow and the second connector.

A second tube is connected to the first tube. The second tube has a first terminal end external to the first tube and an opposed second terminal that is in proximity to the first connector. A breathing bag connects to the second connector and is in fluid communication with the first tube. The breathing bag includes a pressure release valve to the external atmosphere. A third tube provides fluid communication from the external source of oxygen to the second tube. The external source of oxygen is supplying low pressure oxygen to the first tube.

The method includes inserting the patent airway maintaining device into an airway of a patient and coupling the first tube to the patent airway maintaining device such that the patient breathes the oxygen supplied at low pressure. The expiratory gases are flowing from the patient through the patent airway maintaining device into the first tube and the inflatable bag.

The method further includes filtering the inspiratory and expiratory gases. The method further including assisting the breathing of the patient by compressing the breathing bag and redirecting the expiratory gases to inflate the lungs of the patient. The method further including monitoring carbon dioxide in the breathing circuit.

BRIEF DESCRIPTION OF THE DRAWINGS

Preferred embodiments of the invention are described below with reference to the drawings, wherein like numerals are used to refer to the same or similar elements.

DETAILED DESCRIPTION OF THE INVENTION

Figure 1:
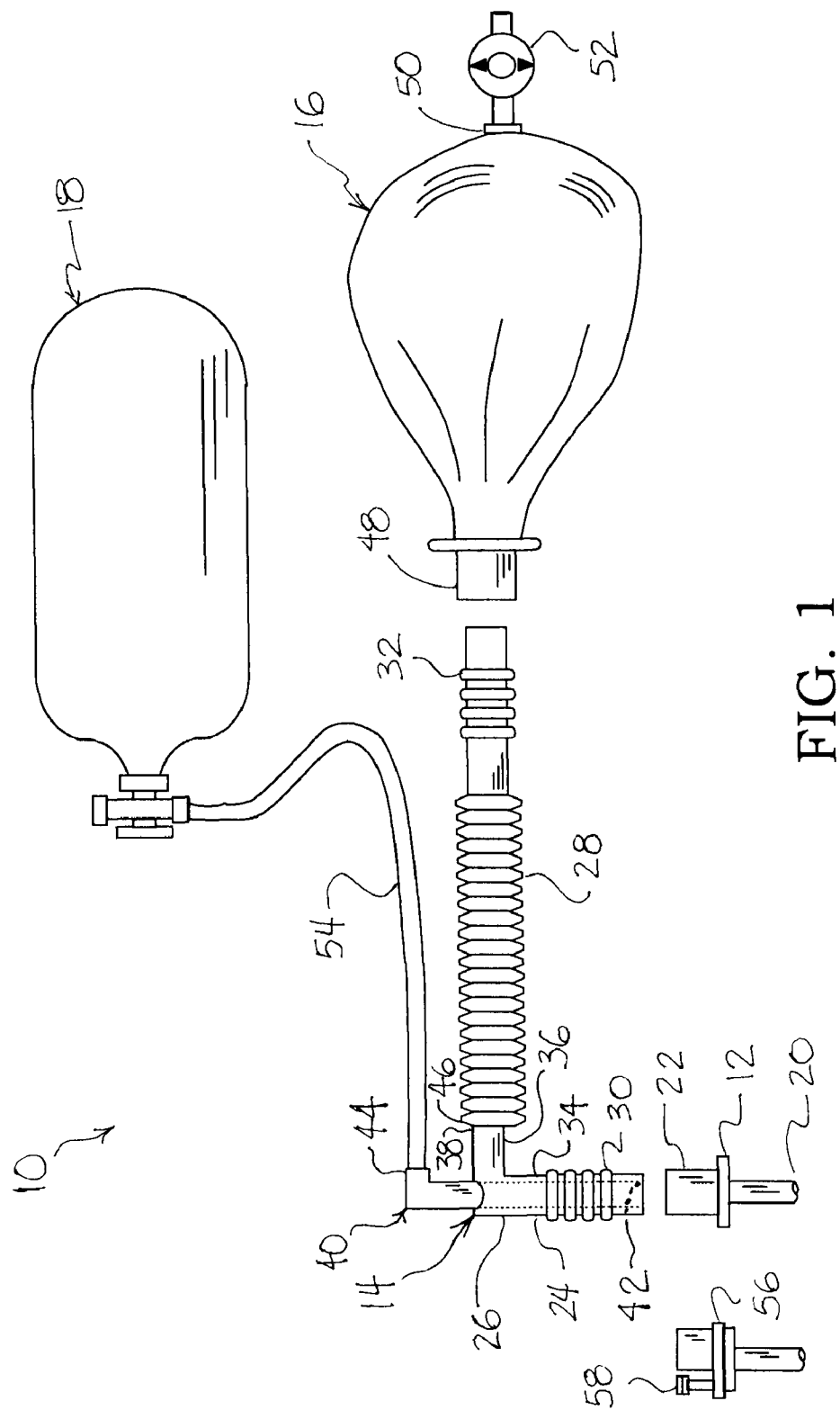
FIG. 1 is a side view of an oxygen breathing circuit constructed in accordance with the present disclosure that can further selectively include an in-line filter.

Referring to the drawings and initially to FIG. 1, breathing circuit 10 includes a patent airway maintaining device 12, a first tube 14 and an inflatable gas bag 16. An external source of oxygen 18 is coupled to tube 14. Breathing circuit 10 combines airway maintaining device 12 with a novel method and structural arrangement of breathing circuit components to supply oxygen at a low pressure to patients.

Patent airway maintaining device 12 is a conventional device for intubation such as, for example, an endo-tracheal tube or a laryngeal mask airway. Airway maintaining device 12 includes a distal end portion 20 and a proximal end portion 22 and has a tubular wall that defines a fluid tight conduit. Distal end portion 20 can have a range of sizes suitable for humans from infants to adults. Proximal end portion 22 has a standard connector for interfacing with first tube 14. The tubular wall of airway maintaining device 12 defines a first central longitudinal axis.

Tube 14 has a wall 24 that defines a fluid tight conduit between airway maintaining device 12 and ventilation bag 16. Tube 14 includes an elbow 26 that has a proximally directed extension 28. Elbow 26 has a distal connector 30 that has a standard interface that provides a fluid tight coupling with proximal end portion 22 of airway maintaining device 12. Extension 28 includes a connector 32 that provides a fluid tight coupling with ventilation bag 16.

Elbow 26 joins a distal first conduit 34 and a proximal second conduit 36 in fluid communication at an angle of approximately 90 degrees. First conduit 34 and connector 30 are aligned with the first central longitudinal axis and airway maintaining device 12. Second conduit 36, connector 32 and extension 28 define a second central longitudinal axis that is preferably perpendicular to the first axis.

Elbow 26 also includes a tube 40 that extends through tubular wall 24 and into first conduit 34. Tube 40 is a conventional conduit that has a first terminal end 42 that is in proximity to connector 30 of first conduit 34 that is aligned with the first longitudinal axis. A second terminal end 44 of tube 40 extends through tubular wall 24 of second conduit 36 to define a port. The portion of tube 40 that exits from tubular wall 24 preferably includes a bend of approximately 90 degrees such that terminal end 44 is approximately aligned with the second longitudinal axis. Terminal end 44 or port 44 can include a fluid tight removable and replaceable cover or cap. Tube 14 can have additional ports that provide a fluid tight connection for the monitoring of carbon dioxide, for example. The tubular wall of tube 40, tubular walls 24 of elbow 26 and connectors 30 and 32 are constructed of a hard or substantially rigid medical grade polymer that is preferably transparent.

Extension 28 is a flexible conduit that has a distal terminal end 46 and an opposed proximal connector 32 that is the proximal end of tube 14. Distal terminal end 46 has a fluid tight connection with the proximal terminal end of second conduit 36 of elbow 26. In contrast to tubular wall 24 of elbow 26, tubular wall 24 of extension 28 is both axially and radially flexible and has a cross-sectional diameter that does not substantially reduce during axial flexing.

In this preferred embodiment, extension 28 is a corrugated, ribbed or pleated flexible tube that is resistant to kinking and approximately three inches in length. Extension 28 preferably has a standard size that is approximately fifteen millimeters in diameter, but it is understood that the diameter of tubular wall 24 of extension 28 can vary depending upon the intended application. Tubular wall 24 of extension 28 is constructed of one or more of a flexible medical grade silicone, rubber or polymer. Distal terminal end 46 of extension 28 is attached to a proximal terminal end 38 of elbow 26 and a proximal terminal end of extension 28 is attached to connector 32 by one or more permanent methods such as heat, adhesives or monolithically formed as a single assembly. Connector 32 is a conventional fluid tight coupling device that provides a standard interface.

Inflatable bag 16 is a conventional breathing bag. Breathing bag 16 has a one liter capacity bag and is preferably made of a soft flexible latex rubber. Inflatable bag 16 has a distal end portion 48 and a proximal end portion 50. Distal end portion 48 includes a standard connector that provides a fluid tight attachment with connector 32 of first tube 14. Proximal end portion 50 includes a pressure release valve 52 that vents the fluid in bag 16 into the environment external to breathing apparatus 10. Pressure release valve 52 is a one way valve that preferably has a variable pressure setting for the flow of gasses from bag 16 to the external environment.

Breathing circuit 10 can selectively include a filter assembly 56. In this preferred embodiment, filter assembly 56 is a conventional in-line filter that is hygroscopic, has a low resistance to flow and can further include bacterial/viral filtration. Filter 56 advantageously humidifies the inspiratory gases as well as filters both the inspiratory and expiratory gasses. In this preferred embodiment, filter assembly 56 includes a port 58 that can be used for the monitoring of carbon dioxide.

Breathing circuit 10 is a low pressure fluid system. A tube 54 provides a fluid tight connection between external source of oxygen 18 and port 44. External source 18 has a flow regulator that provides oxygen at a flow rate of approximately two liters per minute via tube 54 and tube 40 into first conduit 34. It is similarly understood that breathing circuit 10 is constructed for applications that support the low pressure two liter per minute flow rate of oxygen as well as the flow rate of expiratory gases.

Figure 2:
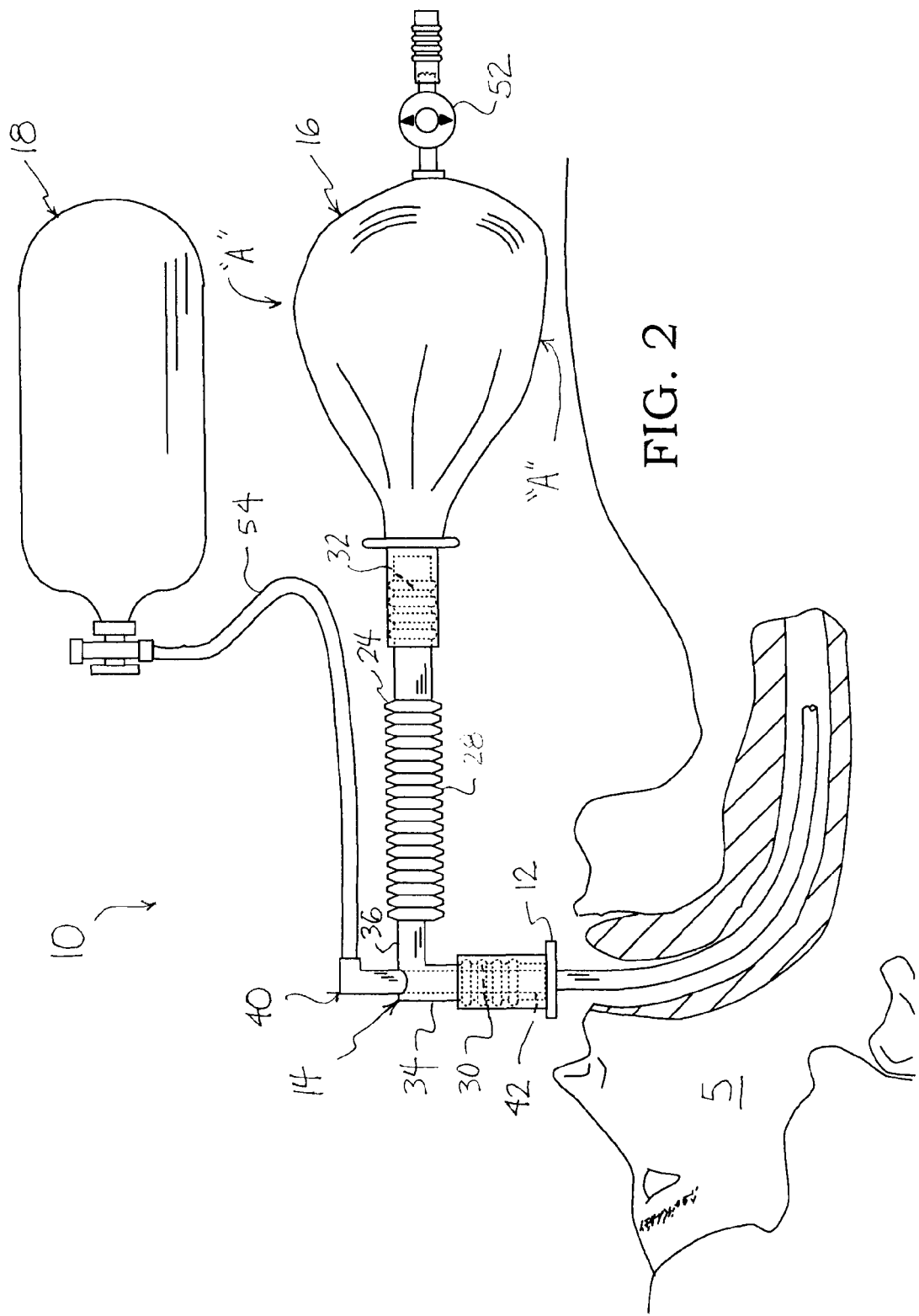
FIG. 2 is a side view of the oxygen breathing circuit of FIG. 1 in use with a patient.

As shown in FIG. 2, in operation a patient 5 is utilizing oxygen breathing circuit 10. Patent airway maintaining device 12 is positioned in and intubates the trachea. Patient 5 can be in deep sedation by intravenous anesthesia prior to or subsequent to the positioning of patent airway maintaining device 12. Tube 14 is in fluid communication with bag 16 and a source of oxygen 18 through tube 40. Conventional filter assembly 56 (FIG. 1) can be selectively coupled to makes a fluid tight connection between patent airway maintaining device 12 and tube 14. Oxygen at a flow rate of approximately two liters per minute is supplied from external source of oxygen 16 through tubes 54 and 40 and exhausts into tube 14 and patent airway maintaining device 12 as an inspiratory gas. The expiratory gases exit through patent airway maintaining device 12, tube 14 and bag 16 as an expiratory gas. Tube 14 provides the essential connectivity to patent airway maintaining device 12 and/or other devices such as the carbon dioxide monitor, tube 40 and bag 16.

Breathing circuit 10 minimizes the risk of dead space by the relatively short length of tube 14 between patent airway maintaining device 12 and bag 16. This advantageously limits the distance that any expiratory gasses have to travel to exhaust through inflatable bag 16. Further, the construction of tubular wall 24 of extension 28 ensures the cross-sectional diameter of tubular wall 24 is substantially maintained during axial flexing and further functions to limit the interruption of flow and/or accumulation of dead space in oxygen breathing system 10. Similarly, the assisted ventilation flow from inflatable bag 16 to patent airway maintaining device 12 has a reduced distance and quicker response time.

The length of flexible tubular extension 28 is sufficient to accommodate the repositioning of bag 16 during a surgical procedure without the risk of collapsing tubular wall 24. This is especially advantageous when a difficult surgical procedure is being performed on the face, for example. In this type of situation, the high level of flexibility of extension 28 of tube 14 accommodates the bending necessary to reposition bag 16 clear of the immediate proximity of the operating field of patient 5 without the risk of substantially reducing the cross-sectional diameter t during axial flexing.

Breathing circuit 10 advantageously uses a novel configuration of tube 14 in breathing circuit 10 that combines the advantageous functions of different materials to a unique application. Tube 14 integrates the rigidity essential for connectors 30, 32 and elbow 26 with the flexibility of a silicone based flexible tubular extension 28. In particular, extension 28 has a limited length that minimizes the risk of dead space and yet has sufficient length to remove bag 16 from being in immediate proximity to the operational field.

When patient 5 is not anesthetized and/or patient 5 is responsive and breathing normally, patient 5 receives oxygen directly through tube 40 into patent airway maintaining device 12 and the trachea. The breathing process of patient 5 is supplemented by the low pressure flow of oxygen from tube 40. The positioning of terminal end 42 within first conduit 34 and in proximity to patent airway maintaining device 12 minimizes any dead space in first tube 14.

The patient 5 exhales through the airway maintaining device 12, filter 56, first tube 14 and into bag 16. Expiratory gases from the patient 5 are effectively precluded from entering into tube 40 due to the pressure from the oxygen source 18. The expiratory gases accumulate in bag 16 until a preset pressure level is reached and one way pressure valve 52 vents the expiratory gasses to the atmosphere external to breathing circuit 10.

When the patient 5 is under anesthesia and/or unresponsive and not breathing normally, the above-identified process for the delivery of oxygen and exhale of the patient 5 is the same, but the inflation of the lungs of the patient is assisted by the active compression of bag 16. At predetermined intervals in time bag 16 is compressed by an external source as shown by arrows "A" and the flow of the expiratory gases is redirected towards the patient 5. The redirected or reversed flow of expiratory gases from bag 16 combines with the oxygen flow from tube 40 in first tube 14 to inflate the lungs of patient 5. The compression of bag 16 can also selectively vent expiratory gases from patient 5 through valve 52. The release of bag 16 after compression creates a vacuum that assists in drawing the expiratory gases from the patient 5 through first tube 14 to bag 16.

Breathing circuit 10 is constructed purely of non-metallic components. This construction advantageously allows breathing circuit 10 to be used in diagnostic machines such as MRI and radiographic devices during diagnostic procedures without degrading or interfering with the diagnostic testing. Patent airway maintaining device 12, central or first tube 14 and bag 16 accompany patient 5 during the diagnostic procedure. Source of oxygen 18 is positioned external to the diagnostic machines and a tube provides low flow oxygen fluid communication to patient 5.

In the preceding specification, the present disclosure has been described with reference to specific exemplary embodiments thereof. It will be evident, however, that various modifications, combinations and changes may be made thereto without departing from the broader spirit and scope of the invention as set forth in the claims that follow. For example, the term patient can encompass other animals as well as humans and correspondingly patent airway maintaining device 12 can be one that is suitable for animals other than humans. In addition, the rigid tubular walled elbow 26, for example, can include one or more variations known in the art such as a rotating connection between tubes 34 and 36, a selectively variable angular relationship between tubes 34 and 36. Similarly, bag 16 can be fabricated of different materials or have alternate capacities. While the present invention is described in terms of a series of embodiments, each embodiment of the present invention can combine one or more novel features of the other embodiments. The specification and drawings are accordingly to be regarded in an illustrative manner rather than a restrictive sense.

What is claimed is:

1. An oxygen breathing circuit that provides low pressure oxygen, the oxygen breathing circuit comprises:
    a first tube that is a fluid tight conduit, the first tube includes a distal elbow and a proximal flexible tubular extension, a distal end portion of the elbow includes a distal connector and a proximal end portion of the flexible tubular extension includes a proximal connector, the distal connector is adapted to couple to a proximal end portion of a patent airway maintaining device, the flexible tubular extension has a cross-sectional diameter that does not substantially reduce during flexing, the flexible tubular extension connected to a proximal end portion of the elbow and terminates in the proximal connector, the flexible tubular extension has an abbreviated length, the elbow, proximal connector and distal connector fabricated of a medical grade non-metallic material, the flexible tubular extension connected to the elbow and the second connector;
    a second tube connected to the first tube, the second tube has a first terminal end external to the first tube and an opposed second terminal end that is in proximity to the first connector;
    a breathing bag that couples to the second connector and is in fluid communication with the patent airway maintaining device, the breathing bag includes a pressure release valve; and
    a third tube that couples an external source of oxygen to the second tube, the external source of oxygen supplying low pressure oxygen to the first tube, the first tube, second tube and third tube constructed for low flow resistance.

2. The oxygen breathing circuit of claim 1, wherein a humidification filter is connected in-line with the breathing circuit between the patent airway maintaining device and the first tube.

3. The oxygen breathing circuit of claim 1, wherein a carbon dioxide monitor is in fluid communication with the breathing circuit.

4. The oxygen breathing circuit of claim 1, wherein the flexible tubular extension is a ribbed silicone polymer based tube and the flexible tubular extension includes a substantially rigid polymer proximal end portion that is a connector.

5. The oxygen breathing circuit of claim 1, wherein the flexible tube has an abbreviated length of approximately three inches.

6. The oxygen breathing circuit of claim 1, wherein the patent airway maintaining device is an endo-tracheal tube.

7. The oxygen breathing circuit of claim 1, wherein the patent airway maintaining device is a laryngeal mask airway.

8. The oxygen breathing circuit of claim 1, wherein the first tube, second tube and third tube reduce dead space.

9. The oxygen breathing circuit of claim 1, wherein the distance between the breathing bag and the patent airway maintaining device has a reduced distance.

10. A method for providing low pressure oxygen to a patient at risk for hypoxia using an oxygen breathing circuit, the method comprising:
    providing an oxygen breathing circuit, the oxygen breathing circuit adapted to connect to
    a patent airway maintaining device,
    a first tube that is a fluid tight conduit, the first tube includes a distal elbow and a proximal flexible tubular extension, a distal end portion of the elbow includes a distal connector and a proximal end portion of the flexible tubular extension includes a proximal connector, the distal connector is adapted to connect to a proximal end portion of the patent airway maintaining device, the flexible tubular extension has a cross-sectional diameter that does not substantially reduce during axial flexing, the flexible tubular extension connected to a proximal end portion of the elbow and terminates in the proximal connector, the elbow, proximal connector and distal connector fabricated of a substantially rigid medical grade non-metallic material, the flexible tubular extension connected to the elbow and the second connector;
    a second tube connected to the first tube, the second tube has a first terminal end external to the first tube and an opposed second terminal that is in proximity to the first connector;
    a breathing bag that connects to the second connector and is in fluid communication with the first tube, the breathing bag includes a pressure release valve to the external atmosphere; and
    a third tube that connects and provides fluid communication from an external source of oxygen to the second tube, the external source of oxygen supplying low pressure oxygen to the first tube, the first tube, second tube and third tube constructed for low flow resistance; and
    inserting the patent airway maintaining device into an airway of a patient and coupling the first tube to the patent airway maintaining device such that the patient breathes oxygen supplied at low pressure and expiratory gases flow through the patent airway maintaining device, first tube and into the inflatable bag.

11. The method for providing an oxygen breathing circuit of claim 10, further including humidifying the inspiratory and expiratory gases of the breathing circuit.

12. The method for providing an oxygen breathing circuit of claim 10, further including assisting the breathing of the patient by compressing the breathing bag and redirecting the expiratory gases and inflating the lungs of the patient.

13. The method for providing an oxygen breathing circuit of claim 10 further including the monitoring of carbon dioxide in the breathing circuit.

14. The method for providing an oxygen breathing circuit of claim 10 further including using the oxygen breathing apparatus during diagnostic procedures using diagnostic equipment.

15. The method for providing an oxygen breathing circuit of claim 10, wherein the step of providing further includes positioning the breathing bag at a reduced distance relative to the patent airway maintaining device, the breathing bag providing a reduced response time.

* * * * *